(12) United States Patent
Lee et al.

(10) Patent No.: US 9,704,224 B2
(45) Date of Patent: Jul. 11, 2017

(54) X-RAY IMAGING APPARATUS AND IMAGE PROCESSING METHOD THEREOF

(71) Applicant: SAMSUNG ELECTRONICS CO., LTD., Suwon-si (KR)

(72) Inventors: Kang Eui Lee, Seoul (KR); Hyun Hwa Oh, Hwaseong-si (KR); Sung Su Kim, Yongin-si (KR); Kye Young Jeong, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 146 days.

(21) Appl. No.: 14/694,504

(22) Filed: Apr. 23, 2015

(65) Prior Publication Data

US 2015/0310602 A1 Oct. 29, 2015

(30) Foreign Application Priority Data

Apr. 23, 2014 (KR) .................. 10-2014-0048480

(51) Int. Cl.
| | |
|---|---|
| *G06K 9/40* | (2006.01) |
| *G06T 5/00* | (2006.01) |
| *A61B 6/00* | (2006.01) |
| *G06T 7/13* | (2017.01) |

(52) U.S. Cl.
CPC ............ *G06T 5/002* (2013.01); *A61B 6/5258* (2013.01); *G06T 5/003* (2013.01); *G06T 7/13* (2017.01); *A61B 6/502* (2013.01); *G06T 2207/10081* (2013.01); *G06T 2207/10088* (2013.01); *G06T 2207/10116* (2013.01); *G06T 2207/20192* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 6,480,300 B1 * | 11/2002 | Aoyama | ................. G06T 5/004 358/1.9 |
| 7,388,621 B2 | 6/2008 | Hsu | |
| 8,130,278 B2 | 3/2012 | Border et al. | |

(Continued)

FOREIGN PATENT DOCUMENTS

| | | |
|---|---|---|
| KR | 100866492 B1 | 11/2008 |
| KR | 1020100077314 A | 7/2010 |

*Primary Examiner* — Sean Conner
(74) *Attorney, Agent, or Firm* — Sughrue Mion, PLLC

(57) ABSTRACT

An X-ray imaging apparatus includes: an X-ray source configured to irradiate X-rays to an object; an X-ray detector configured to obtain a first X-ray image of the object; a noise-reduced image creator configured to generate a noise-reduced image in which a noise is reduced from the first X-ray image; a noise image creator configured to generate a noise image based on differences between the first X-ray image and the noise-reduced image; an edge image creator configured to generate, from the noise image, an edge image in which edges are enhanced; an output image creator configured to combine the noise-reduced image with the edge image to generate a second X-ray image; and a display configured to display the second X-ray image. By enhancing edges while reducing noise, an image with high definition and high quality may be output and a user can obtain accurate information from the image.

20 Claims, 17 Drawing Sheets

(56) References Cited

U.S. PATENT DOCUMENTS

| | | | | |
|---|---|---|---|---|
| 2005/0123184 A1* | 6/2005 | Avinash | ............... | H04N 5/217 382/132 |
| 2008/0298713 A1* | 12/2008 | Yoo | ....................... | G06K 9/40 382/266 |
| 2014/0037222 A1* | 2/2014 | Choudhury | ............ | H04N 19/86 382/235 |
| 2014/0355904 A1* | 12/2014 | Olsson | .................. | G06T 5/004 382/263 |

* cited by examiner

X-RAY IMAGING APPARATUS AND IMAGE PROCESSING METHOD THEREOF

CROSS-REFERENCE TO RELATED APPLICATION

This application claims priority from Korean Patent Application No. 10-2014-0048480, filed on Apr. 23, 2014 in the Korean Intellectual Property Office, the disclosure of which is incorporated herein by reference in its entirety.

BACKGROUND

1. Field

Apparatuses and methods consistent with exemplary embodiments relate to an X-ray imaging apparatus, and an image processing method thereof, and more particularly, to an X-ray imaging apparatus for enhancing edges while reducing noise, and an image processing method of the X-ray imaging apparatus.

2. Description of the Related Art

In the medical imaging equipment that is used to determine existence of lesions related to human's life, detect the locations of lesions, and trace the progress of lesions, for example, in an ultrasonic imaging apparatus, an X-ray imaging apparatus, a computed tomography (CT) scanner, and a magnetic resonance imaging (MRI) apparatus, and the like, the importance of image quality improvement is increasing more and more.

Image quality can be improved by reducing noise in the images and improving definition of images. For example, in order to prevent medical personnel or patients from misinterpreting noise shown on a medical image as a lesion and to enable accurate measurement of the size of a lesion, medical imaging equipment needs to reduce image noise as much as possible and to process lesions and edges of lesions such that they can be clearly shown.

However, when a filter is used to reduce the image noise, edges used to distinguish important parts of the image may be weakened together with the noise reduction. Accordingly, a method of reducing edge deterioration while reducing image noise is needed.

SUMMARY

Exemplary embodiments may address at least the above problems and/or disadvantages and other disadvantages not described above. Also, the exemplary embodiments are not required to overcome the disadvantages described above, and may not overcome any of the problems described above.

One or more exemplary embodiments provide an X-ray imaging apparatus for enhancing edges while reducing noise, and an image processing method of the X-ray imaging apparatus.

In accordance with an aspect of an exemplary embodiment, an X-ray imaging apparatus includes: a noise-reduced image creator configured to create a noise-reduced image in which noise is reduced from the first X-ray image; a noise image creator configured to create a noise image based on differences between the first X-ray image and the noise-reduced image; an edge image creator configured to create an edge image in which edges are enhanced from the noise image; and an output image creator configured to combine the noise-reduced image with the edge image to create the second X-ray image that is output on the display.

The X-ray imaging apparatus may further include a frequency separator configured to separate frequencies of the first X-ray image into low-frequency components and high-frequency components, and to create a low-frequency image corresponding to the low-frequency components and a high-frequency image corresponding to the high-frequency components.

The noise-reduced image creator may create a noise-reduced image in which noise is reduced from the high-frequency image.

The output image creator may combine the low-frequency image, the noise-reduced image, and the edge image to create the second X-ray image.

The edge image creator may perform differentiation on the noise image to create a differential image.

The edge image creator may calculate standard deviation for the noise image to create a standard deviation image.

The edge image creator may multiply the differential image by the standard deviation image to create a first edge filter, and rescale the first edge filter to create a second edge filter.

The edge image creator may multiply the noise image by the second edge filter to create the edge image.

The rescaling may be performed by multiplying each pixel of the first edge filter by a weight value.

The weight value may form an increasing function with respect to a pixel value of the pixel.

The weight value may range from a predetermined value to 1, and the predetermined value may range from 0 to 1.

In accordance with an aspect of an exemplary embodiment, an image processing method of an X-ray imaging apparatus includes: creating a noise-reduced image in which noise is reduced from a first X-ray image created through an X-ray detector; creating a noise image based on differences between the first X-ray image and the noise-reduced image; creating an edge image in which edges are enhanced from the noise image; and combining the noise-reduced image with the edge image to create a second X-ray image that is output on a display.

The image processing method may further include separating frequencies of the first X-ray image into low-frequency components and high-frequency components, and creating a low-frequency image corresponding to the low-frequency components and a high-frequency image corresponding to the high-frequency components.

The creating of the noise-reduced image may include creating a noise-reduced image in which noise is reduced from the high-frequency image.

The creating of the second X-ray image may include combining the low-frequency image, the noise-reduced image, and the edge image to create the second X-ray image.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1A:
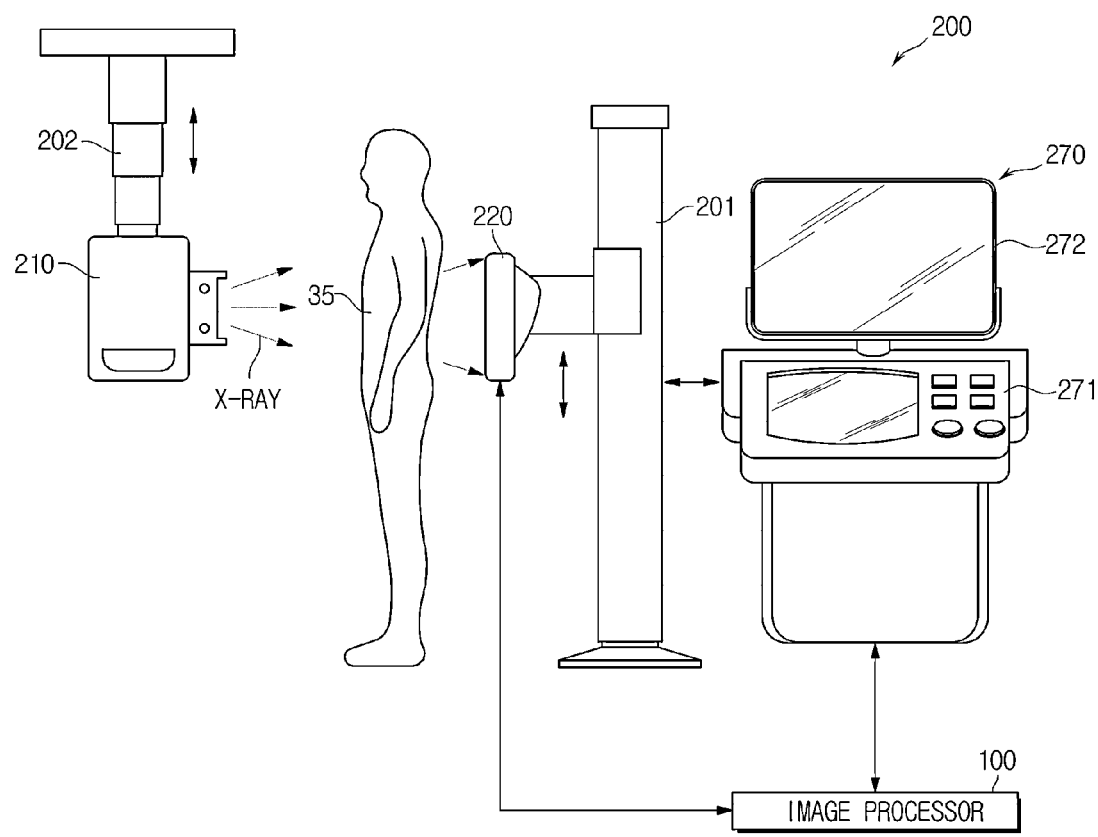
FIG. 1A illustrates an X-ray imaging apparatus.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

There are various X-ray imaging apparatuses that have different structures or use different radiography methods according to regions to be scanned, kinds of X-ray images, or purposes of radiography. Specifically, X-ray imaging apparatuses can be classified into an X-ray apparatus to scan chest, arms, legs, and so on, an X-ray imaging apparatus for mammography to scan breasts, an X-ray imaging apparatus for fluoroscopy, an X-ray imaging apparatus for angiography, an X-ray imaging apparatus for cadiography, and an X-ray imaging apparatus for tomography. The X-ray imaging apparatus according to an exemplary embodiment may be one of the aforementioned X-ray imaging apparatuses or a combination of two or more of the aforementioned X-ray imaging apparatuses.

FIG. 1A illustrates an X-ray imaging apparatus.

Referring to FIG. 1A, an X-ray imaging apparatus 200 may include an X-ray source 210, an X-ray detector 220, and a host device 270.

The X-ray source 210 may generate X-rays and irradiate the generated X-rays onto an object 35 in order to acquire an X-ray image of an object 35.

The object 35 may be a human or an animal, however, the object 35 is not limited thereto. That is, the object 35 may be anything whose internal structure can be visualized by the X-ray imaging apparatus 200.

Also, the object 35 may be a region, which is subject to diagnosis using the X-ray imaging apparatus 200, that is, a region to be scanned with X-rays. Accordingly, in the X-ray imaging apparatus shown in FIG. 1, the object 35 may be a chest, arms, or legs.

The X-ray source 210 may be connected to the ceiling through a holder 202 connected to the upper portion of the X-ray source 210. A length of the holder 202 may be adjustable in an up-down direction. The length of the holder 202 is adjusted so that the location of the X-ray source 210 corresponds to the location of the object 35.

The X-ray detector 220 may be placed to face the X-ray source 210 with the object 35 in between, and detect X-rays irradiated from the X-ray source 210 and then transmitted through the object 35. Also, the X-ray detector 220 may convert the detected X-rays into electrical signals.

One end of the X-ray detector 220 may be connected to a support stand 201 such that the X-ray detector 220 is movable in an up-down direction along the support stand 201. Accordingly, a user can move the X-ray detector 220 in correspondence to the location of the object 35.

As another example, the patient may be placed on a patient table, the X-ray source 210 may be connected to the ceiling and be movable in the length direction of the patient table, and the X-ray detector 220 may be disposed in the patient table such that the X-ray detector 220 is movable in the length direction of the patient table.

The host device 270 may include an input unit 271 to receive a command from a user and a display 272 to display X-ray images, thereby providing a user interface. Herein, the user is a person who diagnoses the object 35 using the X-ray imaging apparatus 200, and may be medical personnel including a doctor, a radiological technologist, and a nurse. However, the user may be anyone who uses the X-ray imaging apparatus 200.

The input unit 271 may include at least one of a switch, a keyboard, a trackball, and a touch screen, however, the input unit 271 is not limited thereto.

The display 272 may be a Cathode Ray Tube (CRT), a Liquid Crystal Display (LCD), or a Light Emitting Diode (LED), however, the display 272 is not limited thereto.

Figure 1B:
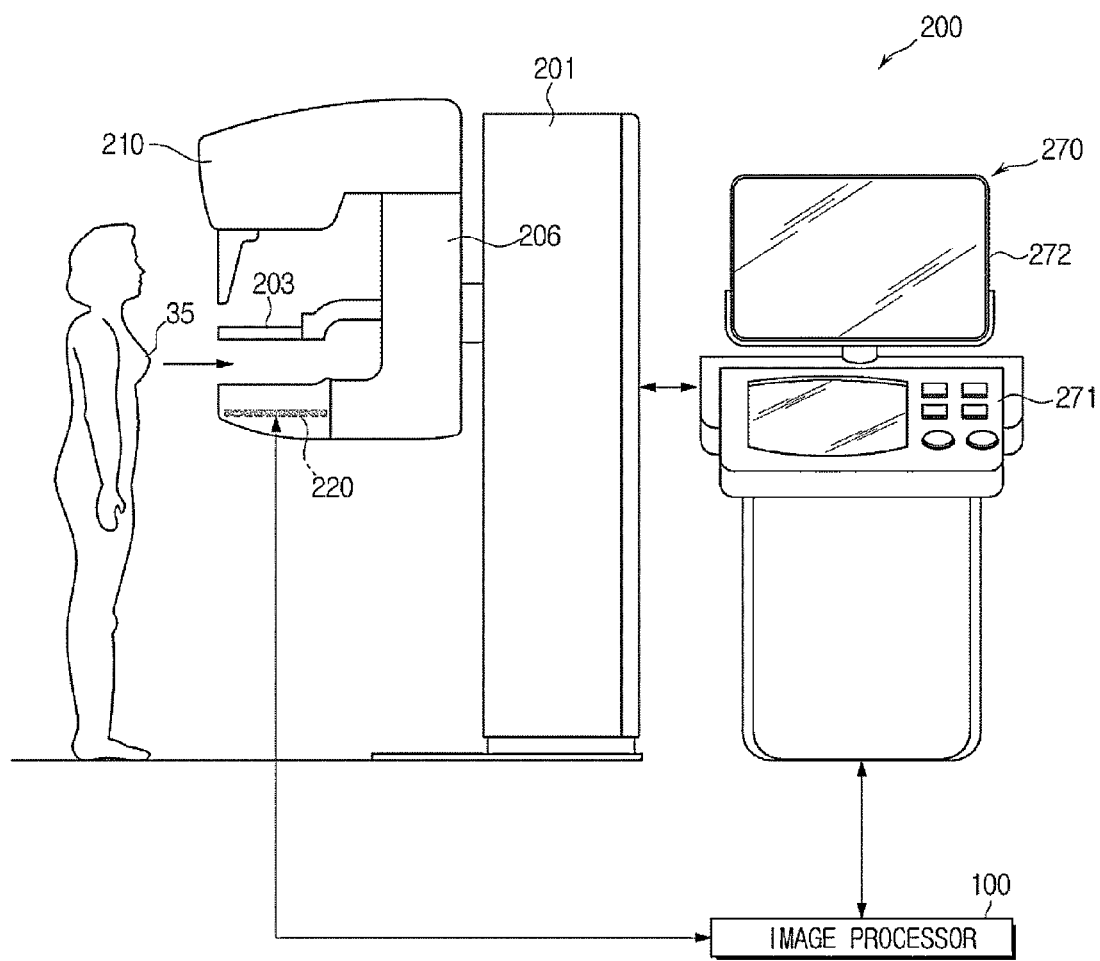
FIG. 1B illustrates an X-ray imaging apparatus for mammography.

FIG. 1B illustrates an X-ray imaging apparatus for mammography.

Referring to FIG. 1B, an X-ray imaging apparatus 200 for mammography may include the X-ray source 210, the X-ray detector 220, and the host device 270, as the X-ray imaging apparatus 200 shown in FIG. 1A.

However, in the case of the X-ray imaging apparatus 200 for mammography, the X-ray source 210 and the X-ray detector 220 may be disposed vertically such that an object 35 can be placed between the X-ray source 210 and the X-ray detector 220 and the X-ray source 210 can irradiate X-rays to the upper part of the object 35.

Also, in the case of the X-ray imaging apparatus 200 for mammography, a pressure paddle 203 to press the object 35 between the X-ray source 210 and the X-ray detector 220 may be further provided. Herein, the object 35 may be a breast, and by pressing the breast using the pressure paddle 203, a clear X-ray image of the object 35 may be acquired.

The pressure paddle 203 may be connected to the frame 206 such that the pressure paddle 203 can be moved in an up-down direction, and by moving the pressure paddle 203, a degree of pressure to be applied to the object 35 may be adjusted.

The X-ray source 210 and the X-ray detector 220 may be connected through the frame 206, and the frame 206 may be connected to the support stand 201 such that the frame 206 can be moved in the up-down direction along the support stand 201 to adjust a height of the frame 206. The height of the frame 206 may be adjusted such that the object 35 is placed between the X-ray source 210 and the X-ray detector 220, more specifically, on the pressure paddle 203 located between the X-ray source 210 and the X-ray detector 220.

Figure 2:
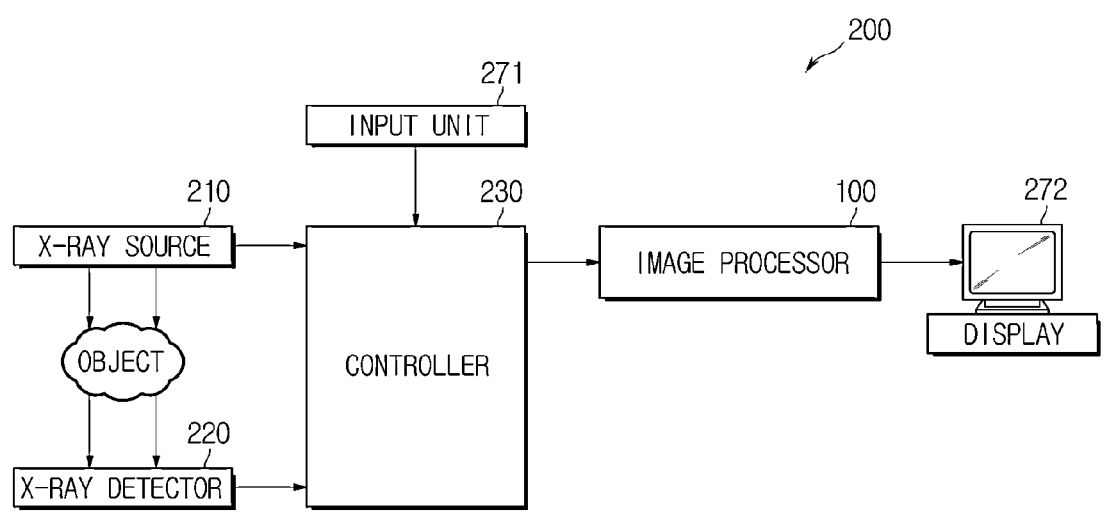
FIG. 2 is a control block diagram of an X-ray imaging apparatus according to an exemplary embodiment.

The X-ray imaging apparatus 200 may acquire an X-ray image of the object 35 through the structure as shown in FIG. 2, perform image processing on the X-ray image, and output the resultant X-ray image.

FIG. 2 is a control block diagram of an X-ray imaging apparatus according to an exemplary embodiment.

Referring to FIG. 2, an X-ray imaging apparatus 200 may include an X-ray source 210, an X-ray detector 220, an image processor 100, a controller 230, an input unit 271, and a display 272.

The X-ray source 210 may be configured to generate X-rays and irradiate the X-rays to an object. The X-ray source 210 may include an X-ray tube in order to generate X-rays. The X-ray tube may be embodied as a two-electrode vacuum tube including an anode and a cathode. A tube body surrounding the anode and the cathode may be a glass tube made of silica (hard) glass or the like. The anode may include a target material applied on the surface of the anode facing the cathode.

If a tube voltage is applied between the cathode and the anode of the X-ray tube, wherein the magnitude of a tube voltage is expressed as a crest value (kVp), thermoelectrons may be accelerated and collide with the target material of the anode, thereby generating X-rays. When the tube voltage increases, velocity of thermoelectrons may increase accordingly. Then, energy (energy of photons) of X-rays that are generated when the thermoelectrons collide with the target material may also increase. According to the application of the tube voltage, a tube current flows in the X-ray tube, wherein the tube current is expressed as an average value (mA). When a tube current increases, a dose of X-rays (that is, the number of X-ray photons) may increase. Accordingly, energy of X-rays can be controlled by adjusting a tube voltage, and a dose of X-rays can be controlled by adjusting a tube current.

The X-ray detector 220 may be configured to detect X-rays irradiated from the X-ray source 210 and then transmitted through the object 35, and to convert the detected X-rays into electrical signals, thereby acquiring an image of the object 35. The X-ray detector 220 may be classified according to its material configuration, a method of converting detected X-rays into electrical signals, and a method of acquiring electrical signals.

For example, the X-ray detector 220 may be classified into a mono type device or a hybrid type device according to its material configuration.

If the X-ray detector 220 is a mono type device, a part of detecting X-rays and generating electrical signals, and a part of reading and processing the electrical signals may be semiconductors made of the same material, or may be manufactured by one process. In this case, a Charge Coupled Device (CCD) or a Complementary Metal Oxide Semiconductor (CMOS) which is a light receiving device may be used.

If the X-ray detector 220 is a hybrid type device, a part of detecting X-rays and generating electrical signals, and a part of reading and processing the electrical signals may be made of different materials, or may be manufactured by different processes. For example, there are cases of detecting X-rays using a light receiving device, such as a photodiode, a CCD, or CdZnTe, and reading and processing electrical signals using a CMOS Read Out Integrated Circuit (CMOS ROIC), of detecting X-rays using a strip detector, and reading and processing electrical signals using a CMOS ROIC, and of using an a-Si or a-Se flat panel system.

The X-ray detector 220 may use a direct conversion mode and an indirect conversion mode according to a method of converting X-rays into electrical signals.

In the direct conversion mode, if X-rays are irradiated, electron-hole pairs may be temporarily generated in a light receiving device, electrons move to an anode, and holes move to a cathode by an electric field applied to both terminals of the light receiving device. The X-ray detector 220 may convert the movements of the electrons and holes into electrical signals. The light receiving device may be made of a-Se, CdZnTe, $HgI_2$, or $PbI_2$.

In the indirect conversion mode, if X-rays irradiated from the X-ray source 70 react with a scintillator to emit photons having a wavelength of a visible light region, the light receiving device may detect the photons, and converts the photons into electrical signals. The light receiving device may be made of a-Si, and the scintillator may be a GADOX scintillator of a thin film type, or a CSI (TI) of a micro pillar type or a needle type.

The X-ray detector 220 may use a Charge Integration Mode (CIM) of storing charges for a predetermined time period and then acquiring a signal from the stored charges, or a Photon Counting Mode (PCM) of counting the number of photons whenever a signal is generated by single X-ray photons, according to a method of acquiring electrical signals.

The X-ray detector 220 may use any of the mono type device, the hybrid type device, the direct conversion mode, and the indirect conversion mode.

The image processor 100 may be configured to receive an image acquired by the X-ray detector 220 through the controller 230, and to perform image processing on the image. According to an exemplary embodiment, the image processor 100 may receive an image directly from the X-ray detector 220. The image received from the controller 230 or the X-ray detector 220 may be defined as an input image.

If the input image is an analog image, the image processor 100 may convert the analog image into a digital image. In order to convert an analog image into a digital image, an analog to digital (A/D) converter may be provided. The image processor 100 may perform image analysis of digitizing an image, or of extracting a specific region, for example, a region of interest (ROI) and determining the size of the specific region.

The image processor 100 may resize or clip an image in order to change the size of an image to be output or to output an image with respect to a specific region such as a ROI. The image processor 100 may remove unnecessary or redundant data from an image to create a compressed image so that the image can be efficiently transmitted or stored.

The image processor 100 may restore image distortion generated by corruption or errors. Also, the image processor 100 may enhance the input image by adjusting the brightness and contrast of the image, removing or reducing noise included in the image, or detecting and enhancing edges.

The image processor 100 may perform additional image processing according to various methods known to those skilled in the art. In the following description, in regard of Noise Reduction (NR) and Edge Enhancement (EE), the configuration and operations of the image processor 100 will be described in detail.

Figure 3:
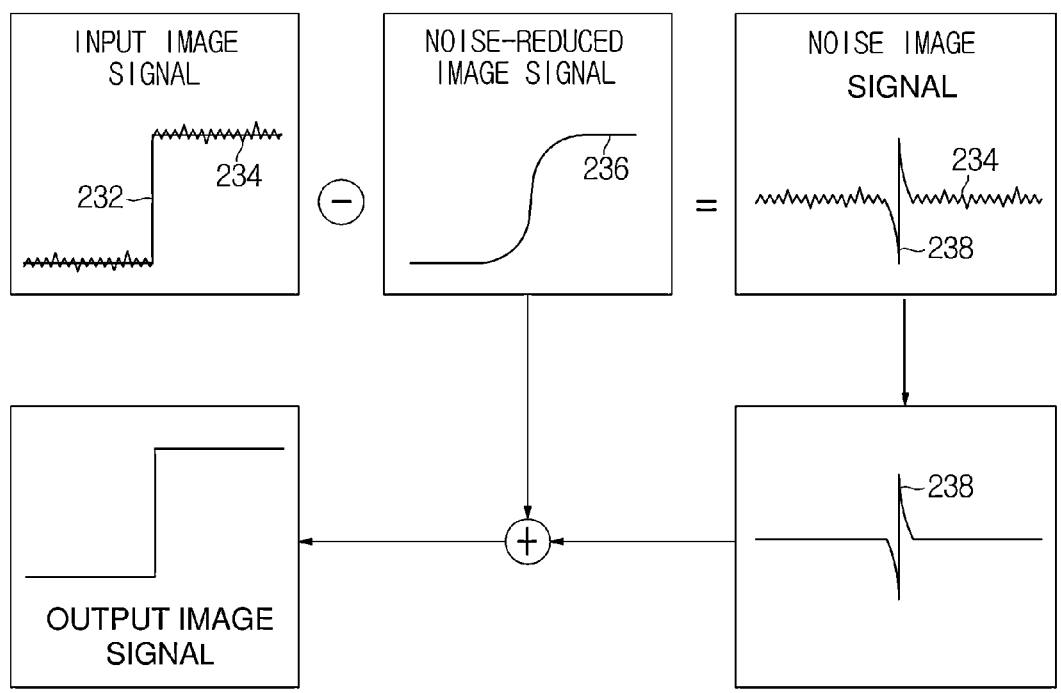
FIG. 3 is a view for describing a process of reducing noise and enhancing edges according to an exemplary embodiment.

FIG. 3 is a view for describing a process of reducing noise and enhancing edges, which is performed by the image processor 100.

When the X-ray detector 220 acquires an input image 200 or when the X-ray detector 220 or the controller 230 transmits an input image, noise may be added to the input image, and then the input image may include a noise signal as well as an original signal corresponding to the internal area of the object 35. As shown in the upper part of FIG. 3, the original input image signal 232 can be expressed as a step function, and the noise signal 234 can be expressed in a zigzag pattern having irregular sizes and distributions interposed on the original input image signal.

The image processor 100 may apply a low-pass filter to the input image in order to reduce noise. If a low-pass filter is applied to the input image, edge signals as well as noise signals may be weakened due to the blurring effect. In other words, edge reduction as well as noise reduction may occur so that the noise-reduced (NR) image signal 236 may have lower edge definition than that of the original input image signal.

In order to enhance the reduced edges, the image processor 100 may acquire a noise image signal including noise signals and edge signal or signals 238 based on differences between the input image and the NR image. As shown in the lower part of FIG. 3, the edge signals may be separated from the noise signals to extract only the edge signals and/or to enhance only the edge signals. Thereafter, the image processor 100 may add the extracted edge signals to the NR image signal, thereby creating an output image signal with enhanced edges. Accordingly, the output image signal may include signals that are similar to the original signals.

The image processor 100 will be described in more detail with reference to FIGS. 4 to 11, below.

Figure 4:
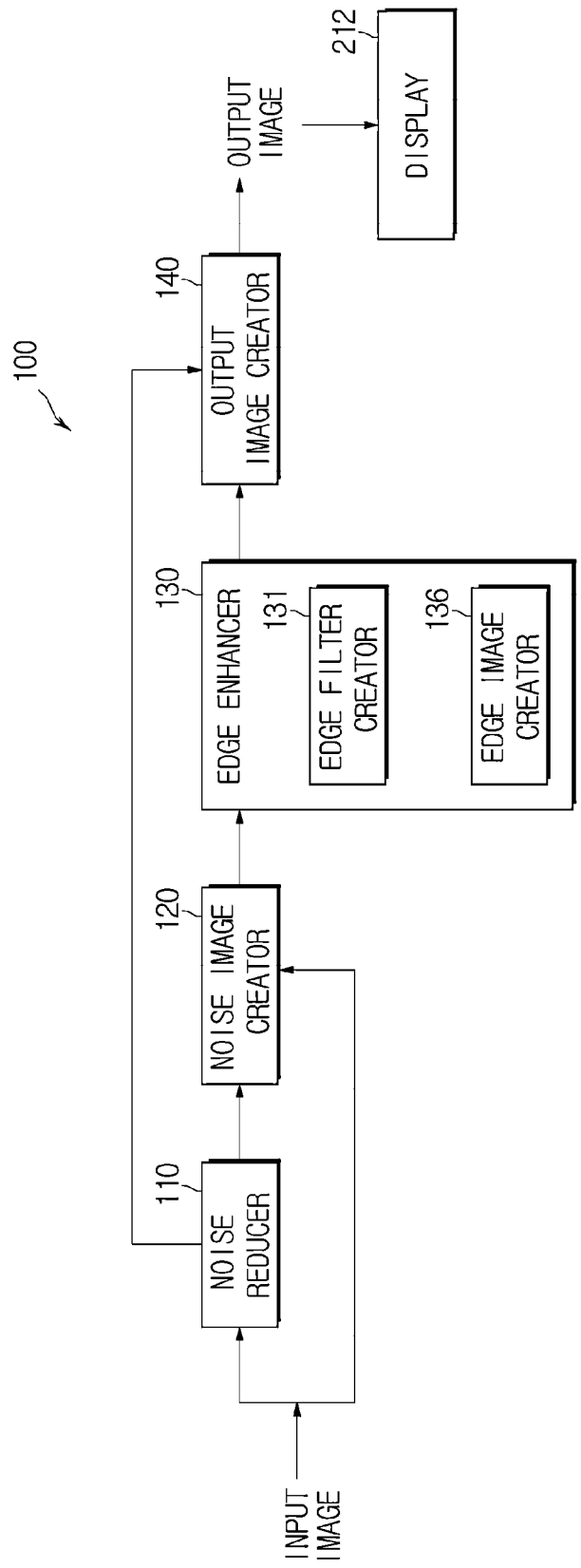
FIG. 4 is a block diagram of an image processor for reducing noise and enhancing edges, according to an exemplary embodiment.

FIG. 4 is a block diagram of the image processor 100 for reducing noise and enhancing edges, according to an exemplary embodiment.

Referring to FIG. 4, the image processor 100 may include a noise reducer 110, a noise image creator 120, an edge enhancer 130, and an output image creator 140.

The noise reducer 110 may reduce noise included in an input image, by using various filters and/or algorithms.

For example, in order to reduce noise arbitrarily generated throughout an input image, i.e., wide-range noise, the noise reducer 110 may use a low-pass filter to apply an average value of peripheral pixels, a sigma filter, a median filter, and/or a Nagao-Matsuyama filter. In order to reduce noise repeatedly generated at regular intervals throughout an input image, i.e., periodic noise, the noise reducer 110 may use a Destriping algorithm or a Debanding algorithm.

As another example, the noise reducer 110 may detect a noise generated area through spatial correlation or radial correlation with respect to noise generated in a region of an input image, i.e., local noise, and reduce the noise using the median filter or the like.

However, the noise reducer 110 may use any other kind of filter or algorithm known to those skilled in the art in order to reduce noise included in an input image. The filters or algorithms may be stored in a storage unit so that the noise reducer 110 can use the filters or algorithms.

The noise image creator 120 may create a noise image based on differences between the input image and the NR image. More specifically, the noise image creator 120 may extract noise and edges from the input image, and create a noise image consisting of the extracted noise and edges.

The edge enhancer 130 may include an edge filter creator 131 and an edge image creator 136, and separate edges from noise in the noise image to enhance the edges. Hereinafter, operations of the edge filter creator 131 and the edge image creator 136 will be described in detail.

Figure 5:
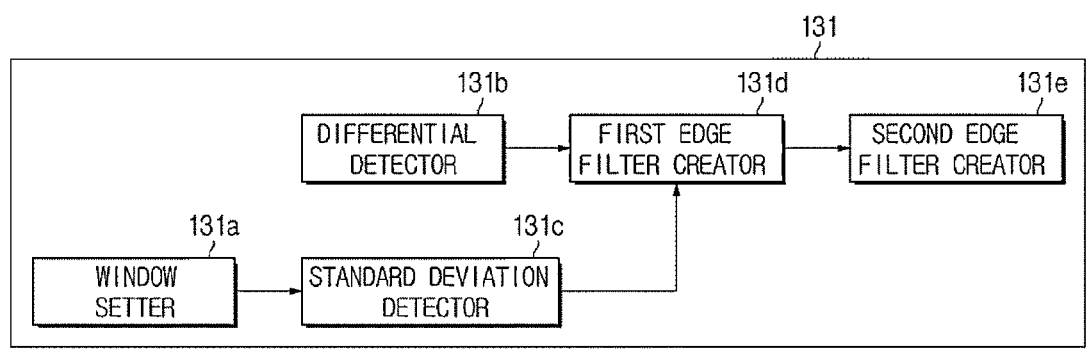
FIG. 5 is a block diagram of an edge filter creator according to an exemplary embodiment.
Figure 6:
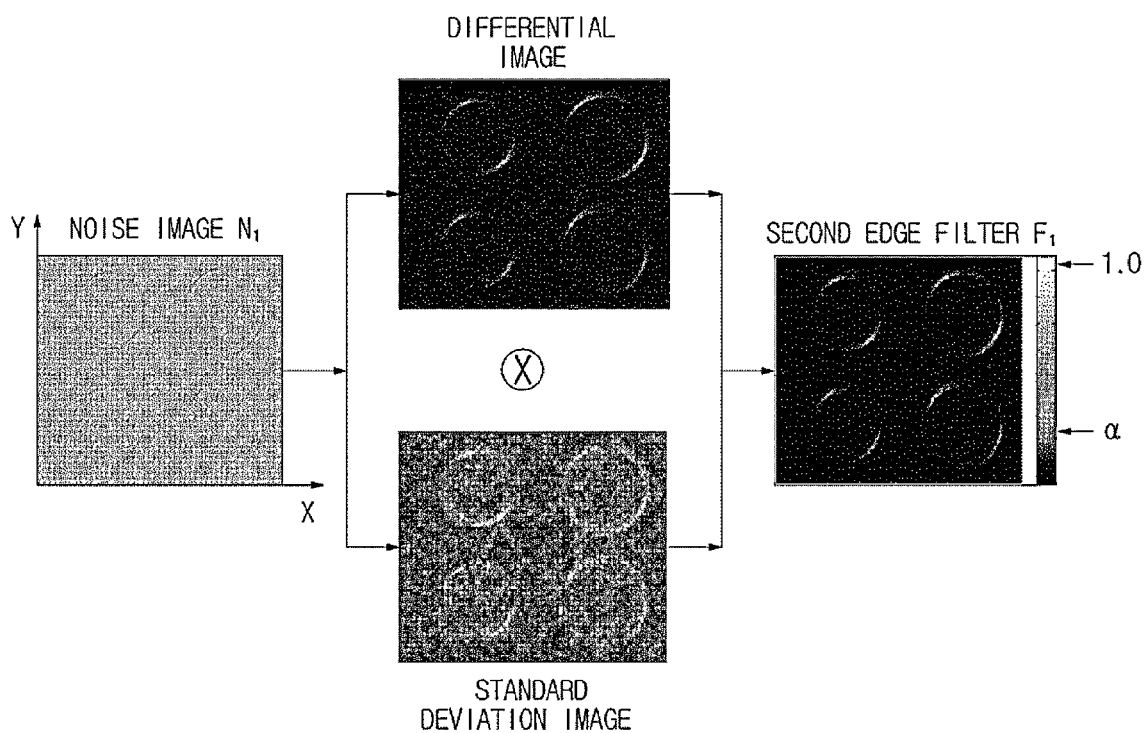
FIG. 6 shows examples of images or filters according to an exemplary embodiment.

FIG. 5 is a block diagram of the edge filter creator 131 according to an exemplary embodiment, and FIG. 6 shows examples of images or filters created by individual components of the edge filter creator 131 shown in FIG. 5.

The edge filter creator 131 may create a filter to separate edges from noise in a noise image, and in order to create the filter, the edge filter creator 131 may include a window setter 131*a*, a differential detector 131*b*, a standard deviation detector 131*c*, a first edge filter creator 131*d*, and a second edge filter creator 131*e*.

The window setter 131*a* may set a window for the noise image so that the noise image can be used by the differential detector 131*a* or the standard deviation detector 131*b*. Herein, the window means a matrix pattern structure that is to be positioned at a predetermined area in the noise image.

The window setter 131*a* may set a window that is to be used by the differential detector 131*a* and a window that is to be used by the standard deviation detector 131*b*, to different sizes. For example, the window setter 131*a* may set a 3×3 window that is to be used by the differential detector 131*a*, and a 5×5 window that is to be used by the standard deviation detector 131*b*.

Also, the window setter 131*b* may set a plurality of windows that are to be used by the differential detector 131, and a plurality of windows that are to be used by the standard deviation detector 131*b*. For example, the window setter 131*b* may set a 1×3 window and a 3×1 window that are to be used by the differential detector 131*a*.

As shown in FIG. 6, the differential detector 131*b* may perform differentiation on a noise image N$_1$ to detect differentiation information, and the standard deviation detector 131*c* may calculate dispersion and standard deviation of the noise image N$_1$ to detect standard deviation information.

More specifically, the differential detector 131*b* may calculate a primary differential value for each pixel of the noise image N$_1$, a secondary differential value for each pixel of the noise image N$_1$, or both a primary differential value and a secondary differential value for each pixel of the noise image N$_1$, and set the calculated value to a pixel value of the corresponding pixel to acquire a new image. The image acquired by the differential detector 131*b* can be defined as a differential image.

Primary differentiation may be performed using a gradient that performs differentiation with respect to x-axis and y-axis directions, that is, using Equation (1) below.

$$\text{Magnitude of Gradient: } |\nabla N| = \sqrt{(d_x)^2 + (d_y)^2}, \quad (1)$$

and $$\text{Direction of Gradient: } D(x, y) = \tan^{-1}\left(\frac{d_y}{d_x}\right),$$

where $$\nabla N = \left(\frac{\partial N}{\partial x}, \frac{\partial N}{\partial y}\right) = (d_x, d_y)$$

In Equation (1), N represents the noise image, ∇ represents the gradient, the magnitude of the gradient is edge strength, and the direction of the gradient is a direction that is perpendicular to an edge direction.

Secondary differentiation may be performed using a Laplacian that can be expressed as Equation (2) below.

$$\nabla^2 N = \frac{\partial^2 N}{\partial x^2} + \frac{\partial^2 N}{\partial y^2} \quad (2)$$

In Equation (2), $\nabla^2$ represents edge strength as a Laplacian.

In other words, the differential detector 131*b* may calculate at least one of a gradient and a Laplacian for each pixel of the noise image to acquire a differential image.

In order to calculate the gradient or the Laplacian, the differential detector 131*b* may use the window set by the window setter 131*a*, a Sobel window, a Prewitt window, a Robert window, a Laplacian window, or a Canny window, which is classified according to window patterns.

The standard deviation detector 131*c* may calculate dispersion or standard deviation for each pixel of the noise image, and set the calculated standard deviation value to a pixel value of the corresponding pixel to create a new image. The image acquired by the standard deviation detector 131*c* can be defined as a standard deviation image.

In order to calculate the dispersion and the standard deviation, the standard deviation detector 131*c* may use the window set by the window setter 131*a*, and a method of calculating standard deviation using a window can be expressed as Equation (3) below.

$$\sigma(m, n) = \sqrt{\frac{1}{P} \sum \sum (w(m, n) - \hat{w}(m, n))^2} \qquad (3)$$

In Equation (3), w represents the window, $\hat{w}$ represents an average value in the window, P represents the number of pixels in the window, and $\sigma$ represents standard deviation.

Referring again to FIG. 6, as the magnitude of a gradient increases in the order of an even region where pixel values little change, a noise region where pixel values change a little, and an edge region where pixel values change significantly, in a noise image $N_1$, pixel values of a differential image also increase in the order of an even region, a noise region, and an edge region, and accordingly, the color of the edge region is most similar to white.

Likewise, as pixel values of a standard deviation image corresponding to standard deviation values also increase in the order of an even region, a noise region, and an edge region, the color of the edge region is most similar to white.

The first edge filter creator 131*d* may create a first edge filter by multiplying the differential image by the standard deviation image. The second edge filter creator 131*e* may rescale the first edge filter to create a second edge filter $F_1$, as described in detail below. The second edge filter creator 131*e* is used to separate edges from noise in the noise image, as described in detail below.

The differential detector 131*b* may differentiate the noise image in one direction such as an x-axis direction or a y-axis direction. In other words, the differential detector 131*b* may obtain a differential value of each pixel, using pixels that are at the left and right or up and down positions of the pixel, in the noise image, to acquire a differential image based on the differential value of each pixel. The standard deviation detector 131*c* may obtain standard deviation of each pixel, using pixels that are positioned diagonally from the pixel, as well as pixels that are at the left, right, up, and down positions of the pixel, in the noise image, to acquire a standard deviation image based on the standard deviation of each pixel. Accordingly, as shown in FIG. 6, a standard deviation image may include more noise information than a differential image, and may also highlight edge information more than the differential image.

The first edge filter creator 131*d* may create a first edge filter using both the differential image and the standard deviation image. However, according to another exemplary embodiment, the standard deviation detector 131*c* may be omitted, and in this case, the first edge filter creator 131*d* may also be omitted.

The second edge filter creator 131*e* may rescale the first edge filter using various functions to create a second edge filter with weakened noise information.

The second edge filter $F_1$ shown in FIG. 6, and the rescaling functions that are used by the second edge filter creator 131*e* will be described with reference to FIGS. 7A to 7C.

Figure 7A:
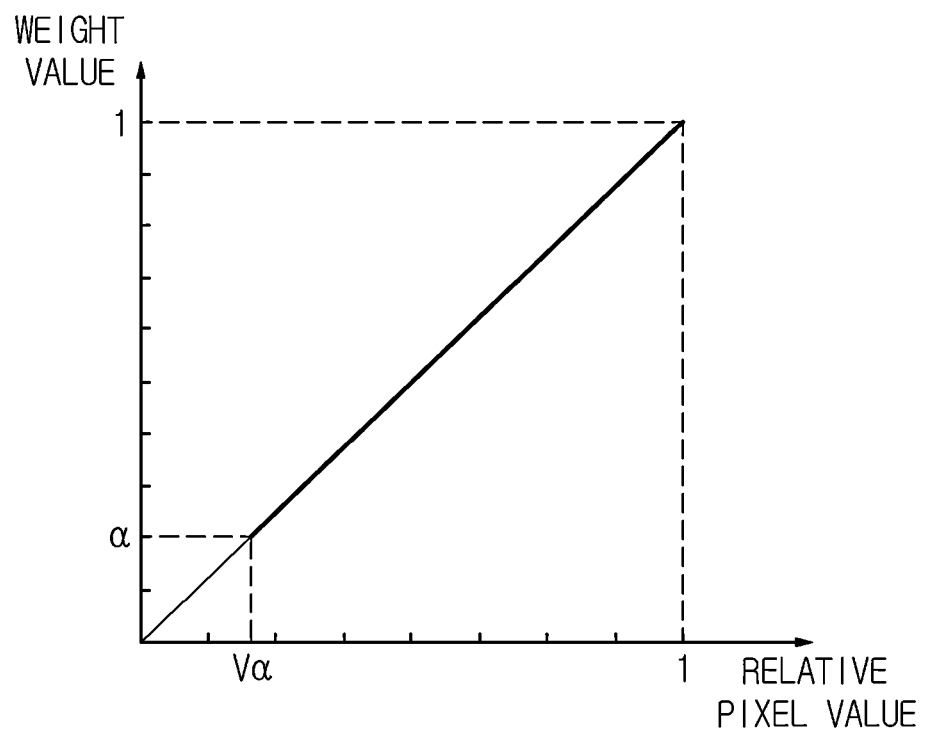
FIGS. 7A, 7B, and 7C show functions that are used for rescaling.
Figure 7B:
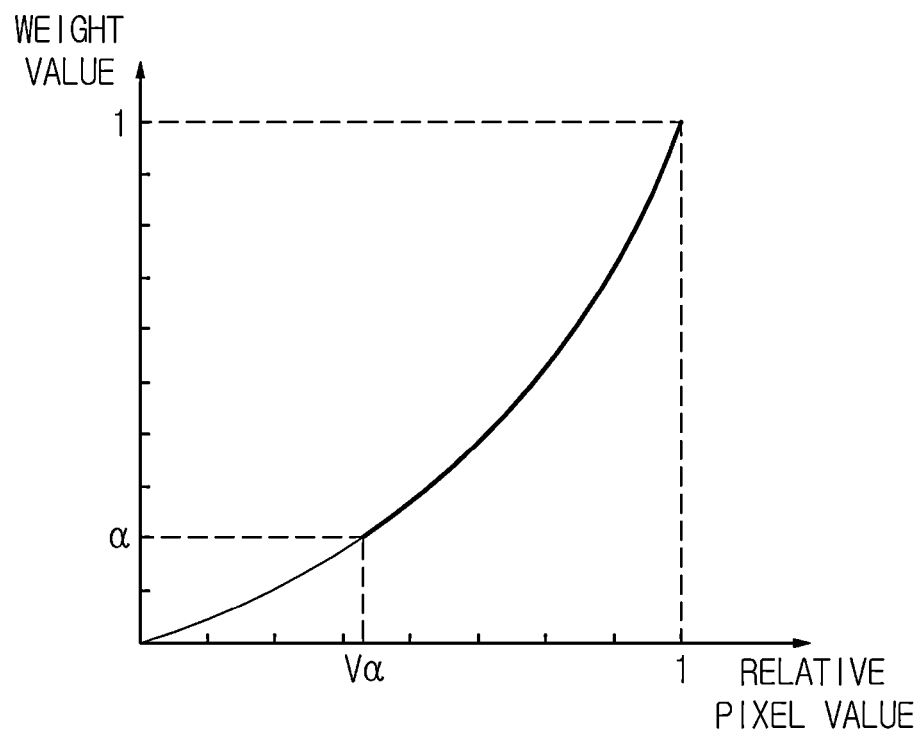
Figure 7C:
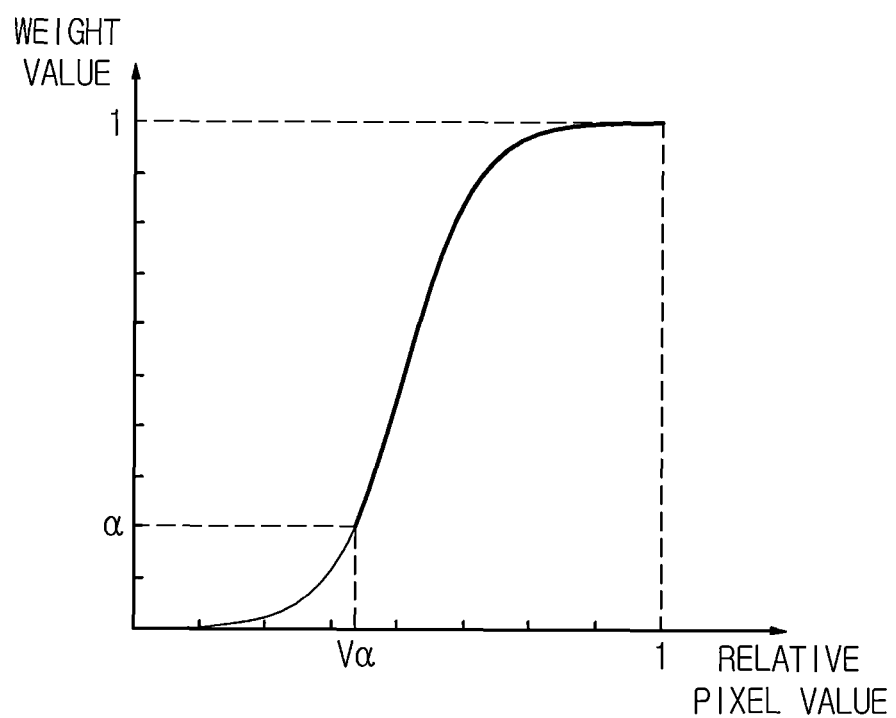

The rescaling functions may include a linear function as shown in FIG. 7A and nonlinear functions as shown in FIGS. 7B and 7C, wherein relative pixel values on the horizontal axis and weight values on the vertical axis form an increasing function.

The weight values for rescaling may range from a to 1, wherein a is defined as a minimum weight value. The minimum weight value $\alpha$ may be selected by a user or set to a predetermined value in advance.

Also, the relative pixel values may be pixel values selected from among a plurality of pixel values of the first edge filter based on a minimum pixel value and a maximum pixel value, and the relative pixel values may range from $V_\alpha$ to 1. For example, it is assumed that the first edge filter consists of a plurality of pixels P1, P2, P3, P4, P5, P6, and P7 and the corresponding pixel values are 30, 45, 50, 80, 160, 200, and 210. In this case, when $V_\alpha$=0.1, the minimum pixel value 30 corresponds to $V_\alpha$ (=0.1), the maximum pixel value 210 corresponds to 1, and the remaining pixel values are rescaled and calculated based on the minimum and maximum pixel values 0.1 and 1. Accordingly, the relative pixel values of the plurality of pixels P1, P2, P3, P4, P5, P6, and P7 become 0.1, 0.175, 0.2, 0.35, 0.75, 0.95, and 1, respectively.

The second edge filter creator 131*e* may calculate a relative pixel value of each pixel of the first edge filter, calculate a weight value of the corresponding pixel using a rescaling function, and then multiply the calculated weight value by an original pixel value of the corresponding pixel, thereby creating the second edge filter. An algorithm to calculate a relative pixel value of each pixel, an algorithm to calculate a weight value corresponding to each pixel, and an algorithm to multiply the weight value by the original pixel value may be pre-stored in a storage unit.

As described above, since the rescaling function is an increasing function, the second edge filter $F_1$ has relatively weakened noise information, as shown in FIG. 6. In other words, the second edge filter $F_1$ has relatively enhanced edge information.

The edge image creator 136 may multiply the noise image by the second edge filter to create an edge image with extracted edges.

Figure 8A:
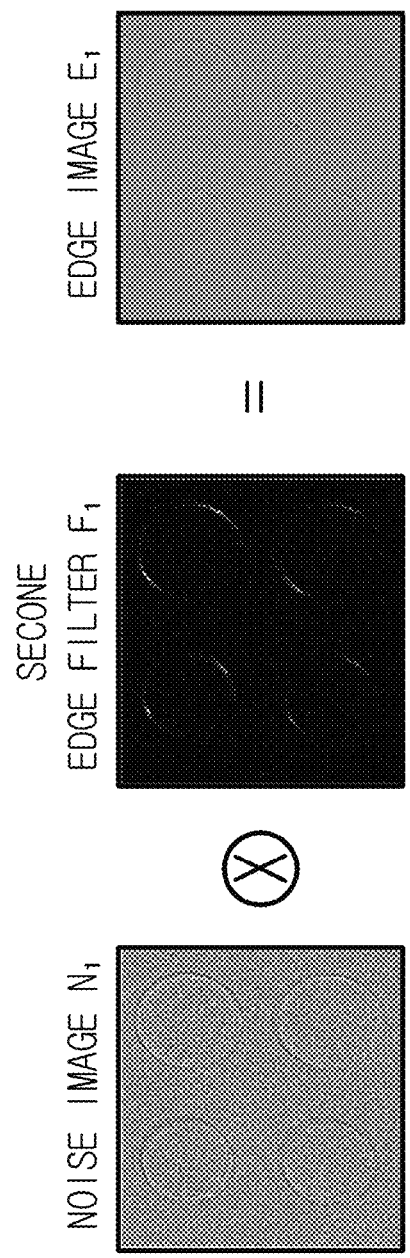
FIGS. 8A and 8B show examples of edge images according to an exemplary embodiment.
Figure 8B:
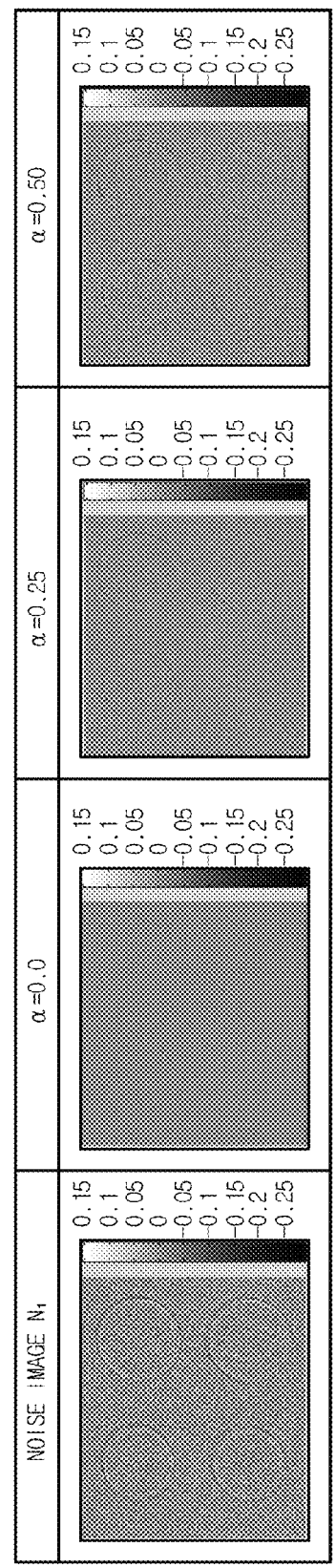

FIGS. 8A and 8B show examples of edge images created by the image processor 100 shown in FIG. 4. A noise image $N_1$ and a second edge filter $F_1$ of FIGS. 8A and 8B are the same as those of FIG. 6. As seen from an edge image $E_1$ of FIGS. 8A and 8B, by multiplying the noise image $N_1$ by the second edge filter $F_1$, edges are separated from noise in the noise image $N_1$, in other words, noise is reduced and edges are enhanced from the noise image $N_1$ to create an edge image $E_1$. A degree of noise reduction and a degree of edge enhancement, that is, a degree of edge extraction with respect to the noise image $N_1$ depends on a minimum weight value for rescaling.

Referring again to FIG. 4, the output image creator 140 may combine the NR image created by the noise reducer 110 with the edge image created by the edge enhancer 130 to create an output image. By combining the NR image with the edge image, edge reduction caused by the blurring effect upon noise reduction of the input image can be restored. Accordingly, the finally created output image becomes an image with reduced noise and enhanced edges, compared to the input image.

Figure 9:
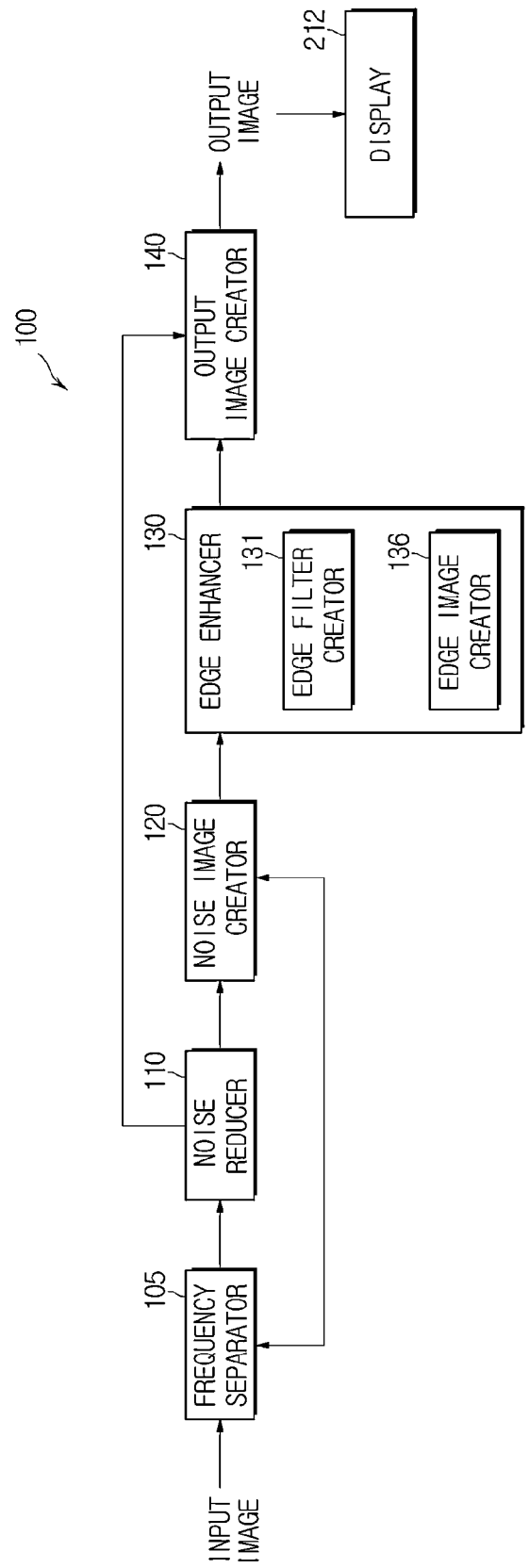
FIG. 9 is a block diagram of an image processor for reducing noise and enhancing edges, according to an exemplary embodiment.

The above description relates to an example in which an input image is transmitted directly to the noise reducer 110, however, as shown in FIG. 9, if the image processor 100 further includes a frequency separator, an input image is subject to frequency separation and then transmitted to the noise reducer 110.

FIG. 9 is a block diagram of an image processor of reducing noise and enhancing edges, according to an exemplary embodiment.

Referring to FIG. 9, an image processor 100 may include a frequency separator 105, a noise reducer 110, a noise image creator 120, an edge enhancer 130, and an output image creator 140.

The frequency separator 105 may separate low-frequency components from high-frequency components in an input image, and create a low-frequency image consisting of the low-frequency components and a high-frequency image consisting of the high-frequency components. Since noise and edges correspond to the high-frequency components, the noise and edges are included in the high-frequency image. A method of separating low-frequency components from high-frequency components is a technique known to those skilled in the art, as for example, a low-pass filter or a high-pass filter. Accordingly, a detailed description for the method of separating low-frequency components from high-frequency components will be omitted.

The low-frequency image created by the frequency separator 105 may be transmitted to the output image creator 140, and the high-frequency image may be transmitted to the noise reducer 110 and the noise image creator 120 in order to create a NR image and a noise image, respectively.

The noise reducer 110 may reduce noise included in the high-frequency image to create a NR image by using a method described above with reference to FIG. 4, in which a high-frequency image is used in place of an input image.

The noise image creator 120 may create a noise image based on differences between the high-frequency image and the NR image. In other words, the noise image creator 120 may extract noise and edges from the high-frequency image, and create a noise image consisting of the extracted noise and edges by using a method described above with reference to FIG. 4, in which a high-frequency image is used in place of an input image.

The edge enhancer 130 may include an edge filter creator 131 and an edge image creator 136 to separate edges from noise in the noise image and to enhance the edges. Since the configurations and operations of the edge filter creator 131 and the edge image creator 136 are the same as described above with reference to FIG. 5, detailed descriptions thereof will omitted.

Figure 10:
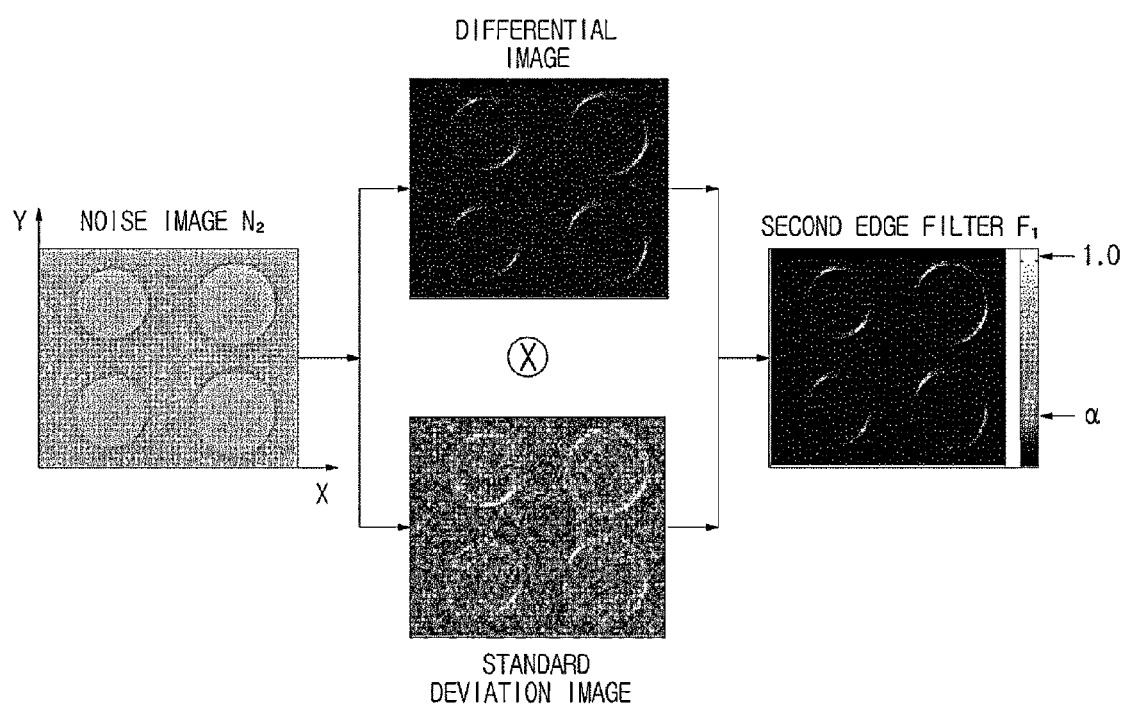
FIG. 10 shows examples of images or filters according to an exemplary embodiment.

FIG. 10 shows examples of images or filters created by individual components of the edge filter creator 131 included in the image processor 100 shown in FIG. 9.

The edge filter creator 131 may create a filter to separate edges from noise in a noise image. In order to separate edges from noise, the edge filter creator 131 may include the window setter 131a, the differential detector 131b, the standard deviation detector 131c, the first edge filter creator 131d, and the second edge filter creator 131e (see FIG. 5).

The window setter 131a may set a window for the noise image to be used by the differential detector 131a or the standard deviation detector 131b. The differential detector 131b may calculate at least one of a gradient and a Laplacian for each pixel of the noise image to acquire a differential image as shown in FIG. 10. Also, the standard deviation detector 131c may calculate dispersion and standard deviation for each pixel of the noise image, and acquire a standard deviation image, as shown in the lower part of FIG. 10, using the standard deviation value as a pixel value of the corresponding pixel.

The first edge filter creator 131d may multiply the differential image by the standard deviation image to create a first edge filter. However, the standard deviation detector 131c may be omitted, and in this case, the first edge filter creator 131d may also be omitted. If the standard deviation detector 131c and the first edge filter creator 131d are omitted, the differential image may be transferred directly to the second edge filter creator 131e.

The second edge filter creator 131e may rescale the first edge filter to create a second edge filter. More specifically, the second edge filter creator 131e may calculate a relative pixel value for each pixel of the first edge filter, calculate a weight value of the corresponding pixel using a rescaling function, and then multiply the weight value by an original pixel value of the corresponding pixel, thereby creating a second edge filter.

As described above, since the rescaling function is an increasing function, a second edge filter $F_2$ may have relatively weakened noise information, as shown in the right part of FIG. 10. In other words, a second edge filter $F_2$ may have relatively strengthened edge information. The second edge filter $F_2$ is used as a filter to separate edges from noise in the noise image.

The edge image creator 136 may multiply the noise image by the second edge filter to create an edge image with extracted edges.

Figure 11:
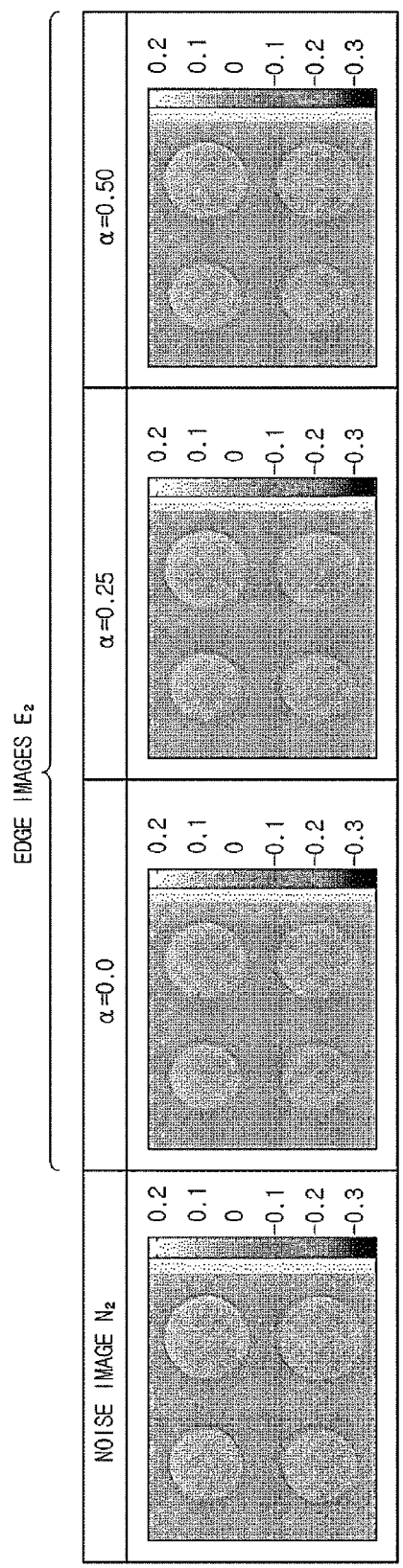
FIG. 11 shows examples of edge images according to an exemplary embodiment.

FIG. 11 shows examples of edge images created by the image processor 100 shown in FIG. 9. As seen from edge images $E_2$ of FIG. 11, by multiplying a noise image $N_2$ by a second edge filter, an edge image $E_2$ in which edges are separated from noise in the noise image $N_2$, in other words, an edge image $E_2$ with reduced noise and enhanced edges may be created. A degree of noise reduction and a degree of edge enhancement with respect to the noise image $N_2$, that is, a degree of edge extraction depends on a minimum weight value $\alpha$ for rescaling.

Referring again to FIG. 9, the output image creator 140 may combine the low-frequency image created by the frequency separator 105, the NR image created by the noise reducer 110, and the edge image created by the edge enhancer 130 to create an output image. By combining the low-frequency image, the NR image, and the edge image, edge reduction caused by the blurring effect upon noise reduction of an input image can be restored. Accordingly, the finally created output image becomes an image with reduced noise and enhanced edges, compared to the input image.

The output image output according to an exemplary embodiment may be displayed on the display 272 so that a user can check the output image.

Referring again to FIG. 2, the controller 230 may control operations of the X-ray imaging apparatus 200. More specifically, the controller 230 may generate a control signal for controlling at least one of the X-ray source 210, the X-ray detector 220, the image processor 100, and the display 272, in response to an instruction or command input through the input unit 271. Also, the controller 230 may generate control signals for controlling the individual components, in response to an instruction or command received through an external device through wired/wireless communication.

The controller 230 may include a storage unit, such as a Read Only Memory (ROM), a Programmable Read Only Memory (PROM), a hard disk, and an optical disk, to store data or algorithms for manipulating the X-ray imaging apparatus 200, and/or the image processor 100.

For example, the storage unit may store various kinds of filters or algorithms that are used by the noise reducer 110 in order to reduce noise of input images or high-frequency images. As another example, the storage unit may store a window set by the window setter 131a, an algorithm to perform differentiation, an algorithm to calculate standard deviation, and an algorithm to multiply a differential image by a standard deviation image.

As still another example, the storage unit may store a minimum weight value $\alpha$, an algorithm that is used by the edge filter creator 131 in order to calculate relative pixel values, an algorithm to calculate a weight value corresponding to each pixel, and an algorithm to multiply the weight value with an original pixel value of the corresponding pixel.

The configurations and operations of the X-ray imaging apparatus 200 and the image processing module 100 are described above only as examples. The image processor 100 may be applied to a different kind of a medical imaging apparatus, such as an ultrasonic imaging apparatus, a CT scanner, and an MRI apparatus, or any other appropriate imaging apparatus that is used in different industrial or technical fields.

Hereinafter, an image processing method of the image processor 100 will be described.

Figure 12:
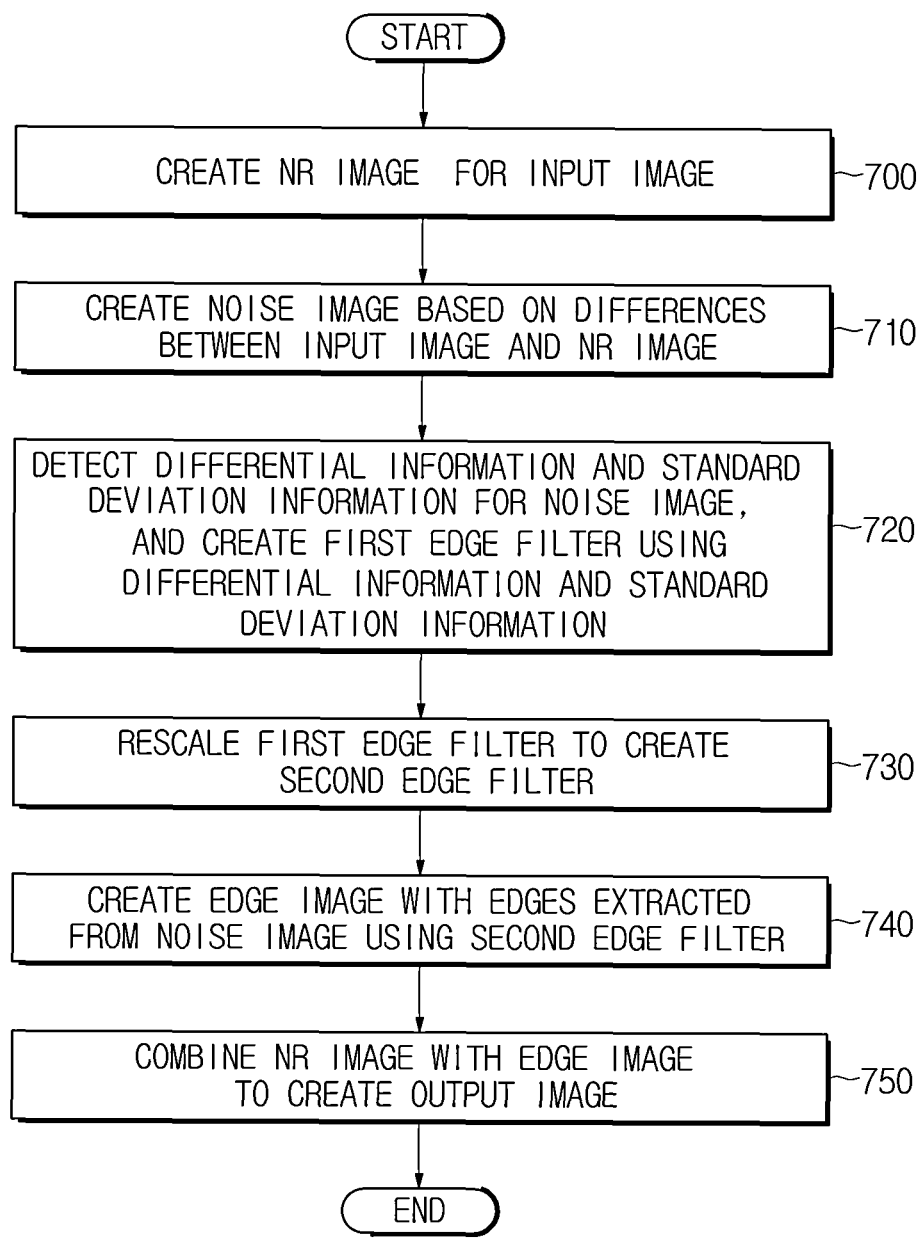
FIG. 12 is a flowchart illustrating an image processing method according to an exemplary embodiment.

FIG. 12 is a flowchart illustrating an image processing method according to an exemplary embodiment.

Referring to FIG. 12, an NR image, which is an image with reduced noise for an input image, may be created, in operation 700.

A noise image may be created based on differences between the input image and the NR image, in operation 710. More specifically, noise and edges may be extracted from the input image, and a noise image consisting of the extracted noise and edges may be created.

Next, differential information and standard deviation information for the noise image may be detected, and a first edge filter may be created using the detected differential information and standard deviation information, in operation 720.

More specifically, a primary differential value for each pixel of the noise image, a second differential value for each pixel of the noise image, or both primary and secondary differential values for each pixel of the noise image may be calculated, and a differential image may be acquired using the calculated value as a pixel value of the corresponding pixel. Then, dispersion and standard deviation for each pixel of the noise image may be calculated, and a standard deviation image may be acquired using the calculated standard deviation value as a pixel value of the corresponding pixel. The differential image may include differential information for the noise image, and the standard deviation image may include standard deviation information for the noise image. When the differential image or the standard deviation image is acquired, a predetermined window may be used.

The differential image may be multiplied by the standard deviation image to create a first edge filter.

The first edge filter may be rescaled to create a second edge filter, in operation 730.

More specifically, a relative pixel value of each pixel of the first edge filter may be calculated using a minimum weight value $\alpha$, and a weight value of the corresponding pixel may be calculated using a rescaling function. The minimum weight value $\alpha$ may range from 0 to 1, and the rescaling function is an increasing function wherein the horizontal axis represents relative pixel values and the vertical axis represents weight values.

The second edge filter may be created by multiplying the calculated weight value by an original pixel value of the corresponding pixel. Since the rescaling function is an increasing function, the second edge filter may have relatively strengthened edge information rather than noise information.

An edge image with edges extracted from the noise image may be created using the second edge filter, in operation 740. In other words, by multiplying the noise image with the second edge filter, an edge image with reduced noise and enhanced edges may be created.

Thereafter, the edge image may be combined with the NR image to create an output image, in operation 750.

By combining the NR image with the edge image, edge reduction caused by to the blurring effect upon noise reduction of the input image can be restored. Through operations 700 to 750, an output image with reduced noise and enhanced edges may be finally created.

Figure 13:
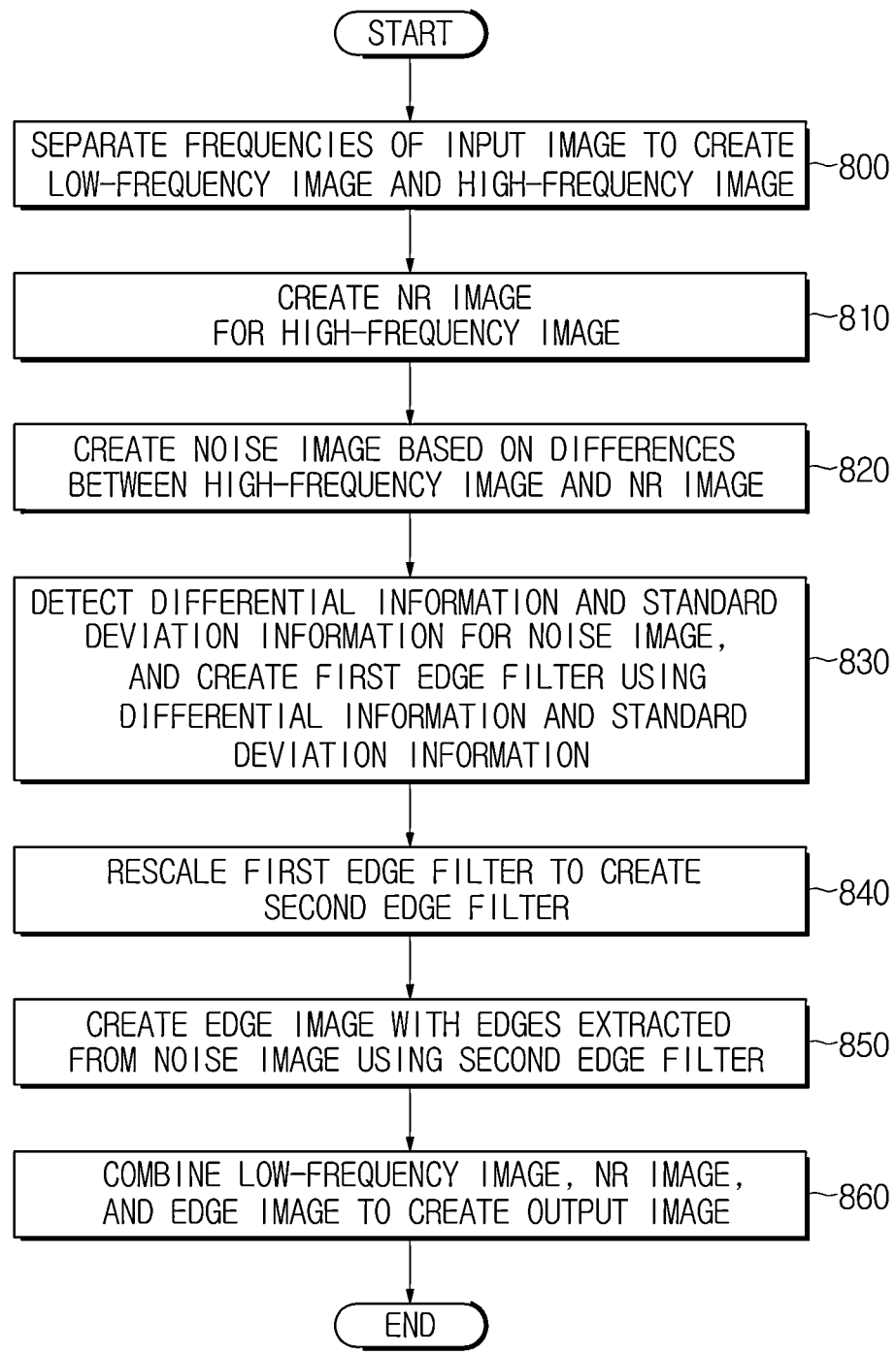
FIG. 13 is a flowchart illustrating an image processing method according to an exemplary embodiment.

FIG. 13 is a flowchart illustrating an image processing method according to an exemplary embodiment.

Frequencies of an input image may be separated to create a low-frequency image and a high-frequency image, in operation 800.

More specifically, low-frequency components may be separated from high-frequency components in an input image, and a low-frequency image consisting of low-frequency components and a high-frequency image consisting of the high-frequency components may be created. Since noise and edges correspond to the high-frequency components, noise and edges may be included in the high-frequency image.

An NR image, which is an image with reduced noise for the high-frequency image, may be created, in operation 810.

A noise image may be created based on differences between the high-frequency image and the NR image, in operation 820.

Next, differential information and standard deviation information for the noise image may be detected, and a first edge filter may be created using the detected differential information and standard deviation information, in operation 830.

More specifically, at least one of a gradient and a Laplacian for each pixel of the noise image may be calculated, and a differential image may be created using the calculated value as a pixel value of the corresponding pixel. Then, dispersion and standard deviation for each pixel of the noise image may be calculated, and a standard deviation image may be acquired using the calculated standard deviation value as a pixel value of the corresponding pixel. The differential image may include differential information for the noise image, and the standard deviation image may include standard deviation information for the noise image. When the differential image or the standard deviation information is acquired, a predetermined window may be used.

The first edge filter may be rescaled using a minimum weight value $\alpha$ and a rescaling function to create a second edge filter, in operation 840. Since the rescaling function is an increasing function, the second edge filter may have relatively strengthened edge information rather than noise information.

An edge image with edges extracted from the noise image may be created using the second edge filter, in operation 850. In other words, by multiplying the noise image by the second edge filter, an edge image may be created.

The low-frequency image, the NR image, and the edge image may be combined to create an output image, in operation 860.

By combining the low-frequency image, the NR image, and the edge image, edge reduction caused by the blurring effect upon noise reduction of the input image can be restored. Through operations 800 to 860, an output image with reduced noise and enhanced edges compared to the input image may be finally created.

According to the X-ray image apparatus and the image processing method described above, by enhancing edges while reducing noise, an image with high definition and high quality may be output. Therefore, a user can obtain or determine accurate information from the output image.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. An X-ray imaging apparatus comprising:
    an X-ray source configured to irradiate X-rays to an object;
    an X-ray detector configured to obtain a first X-ray image of the object by detecting the X-rays having passed through the object;
    an image processor configured to perform image processing on the first X-ray image, and to create a second X-ray image; and
    a display configured to display the second X-ray image, wherein the image processor is configured to generate a noise-reduced image in which a noise is reduced from the first X-ray image, generate a noise image based on differences between the first X-ray image and the noise-reduced image, generate from the noise image, an edge image in which edges are enhanced, combine the noise-reduced image with the edge image to generate the second X-ray image,
    wherein the image processor is further configured to generate the edge image by multiplying a differential image based on a differentiation for the noise image by a standard deviation image based on a standard deviation for the noise image to generate a first edge filter, and rescaling the first edge filter to generate a second edge filter.

2. The X-ray imaging apparatus according to claim 1, wherein the image processor is further configured to separate frequencies of the first X-ray image into low-frequency components and high-frequency components, and to generate a low-frequency image of the first X-ray image corresponding to the low-frequency components and a high-frequency image of the first X-ray image corresponding to the high-frequency components.

3. The X-ray imaging apparatus according to claim 2, wherein the image processor is further configured to create the noise-reduced image in which noise is reduced from the high-frequency image of the first X-ray image.

4. The X-ray imaging apparatus according to claim 3, wherein the image processor is further configured to combine the low-frequency image of the first X-ray image, the noise-reduced image, and the edge image to generate the second X-ray image.

5. The X-ray imaging apparatus according to claim 1, wherein the image processor is further configured to perform the differentiation for the noise image to generate the differential image.

6. The X-ray imaging apparatus according to claim 5, wherein the image processor is further configured to calculate the standard deviation for the noise image to generate the standard deviation image.

7. The X-ray imaging apparatus according to claim 1, wherein the image processor further configured to multiply the noise image by the second edge filter to generate the edge image.

8. The X-ray imaging apparatus according to claim 1, wherein the image processor is further configured to rescale the first edge filter by multiplying each pixel of the first edge filter by a weight value.

9. The X-ray imaging apparatus according to claim 8, wherein the weight value increases as a linear or non-linear function with respect to an increase of a pixel value of the pixel.

10. The X-ray imaging apparatus according to claim 8, wherein the weight value ranges from a predetermined value to 1, and
    the predetermined value ranges from 0 to 1.

11. An image processing method of an X-ray imaging apparatus, the method comprising:
    generating a noise-reduced image in which noise is reduced from a first X-ray image obtained an X-ray detector,
    generating a noise image based on differences between the first X-ray image and the noise-reduced image;
    generating an edge image in which edges are enhanced from the noise image;
    combining the noise-reduced image with the edge image to generate a second X-ray image; and
    outputting the second X-ray image on a display
    wherein the generating the edge image comprises:
        multiplying a differential image based on a differentiation for the noise image by a standard deviation image based on a standard deviation for the noise image to generate a first edge filter; and
        rescaling the first edge filter to generate a second edge filter.

12. The image processing method according to claim 11, further comprising:
    separating frequencies of the first X-ray image into low-frequency components and high-frequency components, and
    generating a low-frequency image of the first X-ray image corresponding to the low-frequency components and a high-frequency image of the first X-ray image corresponding to the high-frequency components.

13. The image processing method according to claim 12, wherein the generating the noise-reduced image further comprises:
    generating the noise-reduced image in which the noise is reduced from the high-frequency image of the first X-ray image.

14. The image processing method according to claim 13, wherein the generating the second X-ray image further comprises:
    combining the low-frequency image of the first X-ray image, the noise-reduced image, and the edge image.

15. The image processing method according to claim 11, wherein the generating the edge image further comprises:
   performing the differentiation on the noise image; and
   generating the differential image based on the performing.

16. The image processing method according to claim 15, wherein the generating the edge image further comprises:
   calculating the standard deviation for the noise image; and
   generating the standard deviation image based on the calculating.

17. The image processing method according to claim 11, wherein the generating the edge image further comprises:
   multiplying the noise image by the second edge filter to generate the edge image.

18. The image processing method according to claim 11, wherein the rescaling further comprises:
   multiplying each pixel of the first edge filter by a weight value.

19. The image processing method according to claim 18, wherein the weight value increases as a linear or non-linear function with respect to an increase in a pixel value of the pixel.

20. The image processing method according to claim 18, wherein the weight value ranges from a predetermined value to 1, and the predetermined value ranges from 0 to 1.

* * * * *